US006197404B1

(12) United States Patent
Varona

(10) Patent No.: US 6,197,404 B1
(45) Date of Patent: Mar. 6, 2001

(54) CREPED NONWOVEN MATERIALS

(75) Inventor: Eugenio Go Varona, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 08/962,992

(22) Filed: Oct. 31, 1997

(51) Int. Cl.$^7$ ................. D06N 7/04; B32B 3/06; B32B 27/02

(52) U.S. Cl. ............. 428/152; 428/198; 428/99; 442/328; 442/398

(58) Field of Search .................. 442/328, 398, 442/394, 401, 400, 170, 171; 428/99, 152, 198; 24/442, 448

(56) References Cited

U.S. PATENT DOCUMENTS

| | | |
|---|---|---|
| 3,668,054 | 6/1972 | Stumpf ................. 161/128 |
| 3,687,754 | 8/1972 | Stumpf ................. 156/72 |
| 3,694,867 | 10/1972 | Stumpf ................. 24/204 |
| 3,705,065 | 12/1972 | Stumpf ................. 156/72 |
| 3,720,554 | 3/1973 | Stumpf ................. 156/62.6 |
| 3,802,817 | 4/1974 | Matsuki et al. . |
| 3,849,241 | 11/1974 | Butin et al. . |
| 3,879,257 | 4/1975 | Gentile et al. . |
| 3,881,490 | 5/1975 | Whitehead et al. . |
| 3,949,128 | * 4/1976 | Ostermeier ............. 428/152 |
| 4,125,659 | * 11/1978 | Klowak et al. ........... 428/153 |
| 4,127,637 | * 11/1978 | Pietreniak et al. ........ 264/114 |
| 4,158,594 | 6/1979 | Becker et al. ........... 162/112 |
| 4,422,892 | * 12/1983 | Plant ................. 156/209 |
| 4,810,556 | 3/1989 | Kobayashi et al. . |
| 4,892,557 | 1/1990 | Conklin et al. . |
| 5,102,724 | 4/1992 | Okawahara et al. . |
| 5,108,820 | 4/1992 | Kaneko et al. . |
| 5,108,827 | 4/1992 | Gessner . |
| 5,270,107 | 12/1993 | Gessner . |
| 5,336,552 | 8/1994 | Strack et al. . |
| 5,382,400 | 1/1995 | Pike et al. . |
| 5,468,796 | 11/1995 | Chen et al. . |
| 5,543,202 | 8/1996 | Clark et al. . |
| 5,614,281 | 3/1997 | Jackson et al. . |
| 5,623,888 | 4/1997 | Zafiroglu . |

FOREIGN PATENT DOCUMENTS

| | | | |
|---|---|---|---|
| 064 853 | 11/1982 | (EP) | ................. D04H/1/54 |
| 0586924 | 3/1994 | (EP) . | |
| 97 19808 | 6/1997 | (WO) | ................. B32B/5/02 |

OTHER PUBLICATIONS

Polymer Blends and Composites by John A. Manson and Leslie H. Sperling, Copyright 1976, by Plenum Press, a division of Plenum Publishing Corporation of New York, IBSN 0–306–30831–2, pp. 273–277.

Capillary Sorption Equilibria in Fiber Masses by A.A. Burgeni and C. Kapur, Textile Research Journal, vol. 37 pp. 356–366, (1967).

"A refined method to evaluate diapers for effectiveness in reducing skin hydration using the adult forearm"; Frank J. Akin, Jac T. Lemmen, Dena L. Bozarth, Martin J. Garofalo and Gary L. Grove; Skin Research and Technology 1997:3: 173–176.

* cited by examiner

Primary Examiner—Terrel Morris
Assistant Examiner—Cheryl Juska
(74) Attorney, Agent, or Firm—Pauley Petersen Kinne & Fejer

(57) ABSTRACT

A creped nonwoven web having permanent crepe includes regions of interfilament bonding which are permanently bent out-of-plane, alternating with regions of no interfilament bonding. The non-bonded regions include a multiplicity of filament loops which terminate at both ends in the creped interfilament-bonded regions. The creped nonwoven web is useful as the female component of a hook-and-loop fastener, and can also be used in diaper outercovers, liners, transfer and surge layers, wipers, and other fluid handling products.

40 Claims, 4 Drawing Sheets

CREPED NONWOVEN MATERIALS

FIELD OF THE INVENTION

This invention relates to permanently creped nonwoven materials having low density, high permeability, improved loft and softness, looping, and out-of-plane fiber orientation.

BACKGROUND OF THE INVENTION

Creped thermoplastic nonwoven materials are known from U.S. Pat. No. 4,810,556, issued to Kobayashi et al. In the disclosed process, a raw nonwoven fabric is coated with a lubricant and then pressed between a drive roll and a plate having a rough sandpaper-like surface. The plate is positioned near the drum and is substantially parallel or tangential to the outer surface of the drum. The raw nonwoven fabric is crinkled in a wavelike fashion in the direction of movement of the fabric by the frictional force caused by the pressing. The resulting creped fabric has wavelike crepes which contribute to softness. However, the creping accomplished by this process is not believed to be permanent. It is believed that the creping accomplished by this process can be removed or reduced significantly by subjecting the nonwoven web to mechanical stretching sufficient to flatten out the wavelike crepes. Also, the creping is naturally reduced over time during use of the fabric.

The creping of paper is also known in the art. However, paper has traditionally been creped using processes different from those used to crepe thermoplastic nonwoven webs. U.S. Pat. No. 3,879,257, issued to Gentile et al., discloses a process used for producing creped paper. A bonding material, preferably elastomeric, is applied to first and second surfaces of the paper so that it covers from about 15–60% of both paper surfaces and penetrates into about 10–40% of the paper thickness from both surfaces. Then, one side of the paper is adhered to a creping surface, such as a creping drum, using the bonding material to cause the adhesion. Then, the paper is creped from the creping surface using a doctor blade positioned at an angle to the surface. This creping method greatly disrupts the fibers in the unbonded regions of the paper increasing the overall softness, absorbency and bulk of the paper, and finely crepes the bonded areas of the paper to soften them.

There is a need or desire for a creped thermoplastic nonwoven web in which some or portions of the fibers are greatly disrupted to cause permanent creping. There is also a need or desire for a permanently creped nonwoven web containing individual filament loops, suitable for use as the female component in a hook-and-loop fastener.

SUMMARY OF THE INVENTION

The present invention is a permanently creped thermoplastic nonwoven web having interfilament bonded areas which are bent or oriented permanently out of plane, unbonded areas between the bonded areas, and substantial filament looping in the unbonded areas. The permanently creped web has low density, high permeability and excellent softness, and is useful as a loop material for a hook and loop fastener. The web also has a crinkled, puckered texture, and is useful for liners, transfer and surge layers, outercovers, wipes, and other fluid handling products.

The starting material used to make the invention is an uncreped thermoplastic nonwoven web which can, for instance, be a thermoplastic spunbonded web or a thermoplastic meltblown web. The nonwoven web is at least partially coated on one side with an adhesive, so that about 5–100% (preferably 10–70%) of the total surface area on one side is coated, and about 0–95% (preferably 30–90%) of the area is uncoated. The nonwoven web also possesses interfilament bonding, in the form of a pattern called the "nonwoven web bond pattern," which is imparted during manufacture of the nonwoven web. The adhesive penetrates the nonwoven web to some extent in the coated areas, causing increased interfilament bonding in those areas. The at least partially coated side of the thermoplastic nonwoven web is then placed against a creping surface, such as a creping drum, and is peelably bonded to the creping surface. The creping surface is preferably heated, and is moved (e.g. rotated) in a machine direction. As the creping surface moves, the leading edge of the nonwoven web bonded to the surface is creped off using a doctor blade.

The doctor blade penetrates the adhesive coating underneath the web and lifts the nonwoven web off the drum, resulting in permanent filament bending in the bonded areas corresponding to the nonwoven web bond pattern, and permanent looping of the filaments in the unbonded areas. Only one side of the web need be creped in this fashion to form a loop material suitable for use as the female component in a hook and loop fastener. Alternatively, both sides of the web may be creped by applying the adhesive on the second surface of the web as well as the first, adhering the second surface of the web to the same or a different creping surface, and creping the second side of the web from the creping surface using a doctor blade.

With the foregoing in mind, it is a feature and advantage of the invention to provide a permanently creped nonwoven web having low density, high permeability and excellent softness and texture.

It is also a feature and advantage of the invention to provide a permanently creped nonwoven web having a looped structure suitable for use as the female component of a hook and loop fastener.

It is also a feature and advantage of the invention to provide a permanently creped nonwoven web having a textured surface suitable for use in liners, transfer and surge layers, outercovers, wipers, and other fluid handling materials.

The foregoing and other features and advantages of the invention will become further apparent from the following detailed description of the presently preferred embodiments, read in conjunction with the accompanying drawings. The detailed description and drawings are intended to be merely illustrative rather than limiting, the scope of the invention being defined by the appended claims and equivalents thereof.

DEFINITIONS

Figure 1:
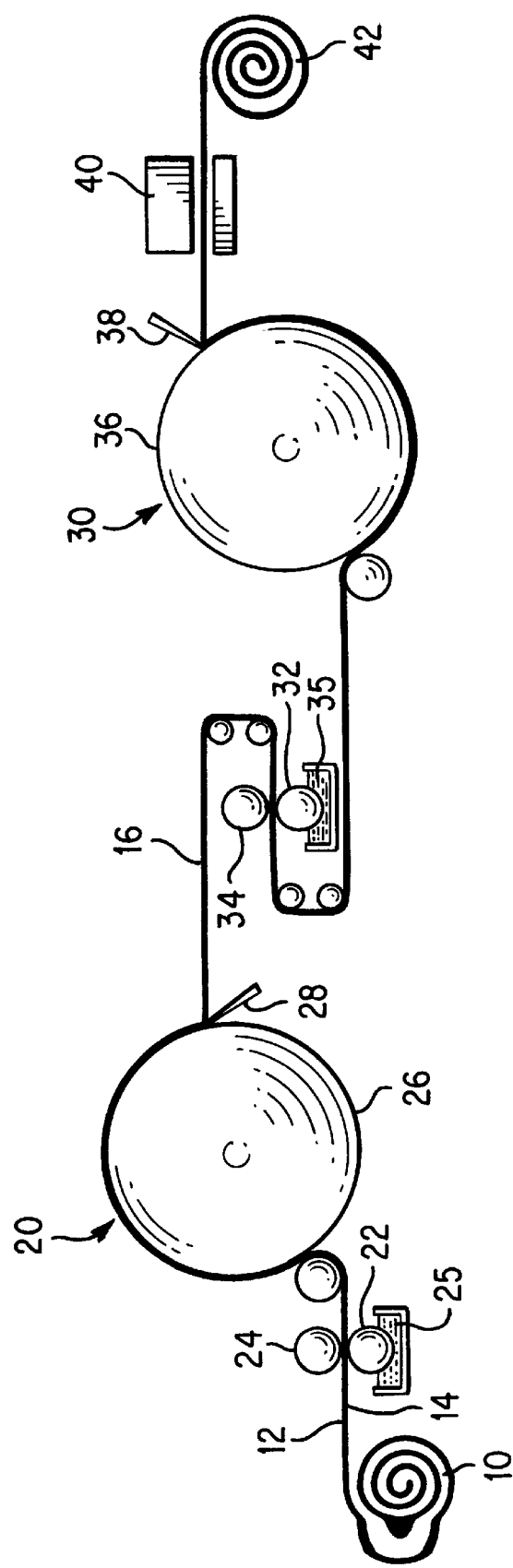
FIG. 1 is a schematic side view of one type of an apparatus for producing a permanently creped nonwoven web of the invention.

"Permanently creped" refers to a creped nonwoven web having bonded and unbonded areas, in which the bonded areas are permanently bent out-of-plane and the unbonded portions are permanently looped, such that the nonwoven web cannot be returned to its original uncreped state by applying a mechanical stress.

"Crepe level" is a measure of creping and is calculated according to the following equation:

$$\text{Crepe level (\%)} = \frac{\text{Speed of Creping Surface minus speed of windup reel for the creped web}}{\text{Speed of Creping Surface}} \times 100$$

"Bent out-of-plane" refers to a bonding or orientation of portions of the nonwoven web in a direction away from the plane in which the nonwoven web substantially lies before being subjected to the creping process. As used herein, the phrase "bent out-of-plane" generally refers to nonwoven webs having creped portions bent at least about 15 degrees away from the plane of the uncreped nonwoven web, preferably at least about 30 degrees.

"Looped" refers to unbonded filaments or portions of filaments in a creped nonwoven web which define an arch, semi-circle or similar configuration extending above the plane of the uncreped nonwoven web, and terminating at both ends in the nonwoven web (e.g. in the bonded areas of the creped nonwoven web).

"Nonwoven web" means a web having a structure of individual fibers or threads which are interlaid, but not in an identifiable, repeating manner. Nonwoven webs have been, in the past, formed by a variety of processes such as, for example, melt-blowing processes, spunbonding processes and bonded carded web processes.

"Nonwoven web bond pattern" is a pattern of interfilament bonding in the nonwoven web which is imparted during manufacture of the nonwoven web.

"Meltblown fibers" means fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameter, possibly to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, the disclosure of which is hereby incorporated by reference.

"Microfibers" means small diameter fibers having an average diameter not greater than about 100 microns, for example, having an average diameter of from about 0.5 microns to about 50 microns, or more particularly, an average diameter of from about 4 microns to about 40 microns.

"Spunbonded fibers" refers to small diameter fibers which are formed by extruding a molten thermoplastic material as filaments from a plurality of fine, usually circular, capillaries of a spinnerette with the diameter of the extruded filaments then being rapidly reduced as by, for example, eductive drawing or other well-known spunbonding mechanisms. The production of spunbonded nonwoven webs is illustrated in patents such as, for example, in U.S. Pat. No. 3,802,817 to Matsuki et al. and U.S. Pat. No. 5,382,400 to Pike et al. The disclosures of these patents are hereby incorporated by reference.

"Polymer" generally includes, but is not limited to, homopolymers, copolymers, such as, for example, block, graft, random and alternating copolymers, terpolymers, etc. and blends and modifications thereof. Furthermore, the term "polymer" shall include all possible geometrical configurations of the material. These configurations include, but are not limited to, isotactic, syndiotactic and random symmetries.

"Bicomponent fibers" refers to fibers which have been formed from at least two polymers extruded from separate extruders but spun together to form one fiber. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another or may be a side-by-side arrangement or an "islands-in-the-sea" arrangement. Bicomponent fibers are taught in U.S. Pat. No. 5,108,820 to Kaneko et al., U.S. Pat. No. 5,336,552 to Strack et al., and European Patent 0586924. For two component fibers, the polymers may be present in ratios of 75/25, 50/50, 25/75 or any other desired ratios.

"Biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

"Blend" means a mixture of two or more polymers while the term "alloy" means a sub-class of blends wherein the components are immiscible but have been compatibilized. "Miscibility" and "immiscibility" are defined as blends having negative and positive values, respectively, for the free energy of mixing. Further, "compatibilization" is defined as the process of modifying the interfacial properties of an immiscible polymer blend in order to make an alloy.

"Consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, particulates and materials added to enhance processability of the composition.

DETAILED DESCRIPTION OF THE PRESENTLY PREFERRED EMBODIMENTS

FIG. 1 illustrates a process for preparing a creped nonwoven web of the invention, which can be a creped spunbonded web, and which can be creped on one or both sides. A nonwoven web 12, which can be a spunbonded web, is unwound from a supply roll 10. The nonwoven web 12 may be passed through a first creping station 20, a second creping station 30, or both. If it is desired to crepe the nonwoven web 12 on only one side, it may be passed through either the first creping station 20 or the second creping station 30, with one creping station or the other being bypassed. If it is desired to crepe the nonwoven web 12 on both sides, it may be passed through both creping stations.

A first side 14 of the web 12 may be creped using the first creping station 20. The creping station 20 includes first a printing station including a lower patterned or smooth printing roller 22, an upper smooth anvil roller 24, and a printing bath 25, and also includes a dryer roller 26 and associated creping blade 28.

The rollers 22 and 24 nip the web 12 and guide it forward. As the rollers 22 and 24 turn, the patterned or smooth printing roller 22 dips into bath 25 containing an adhesive material, and applies the adhesive material to the first side 14 of the web 12 in a partial coverage at a plurality of spaced apart locations, or in a total coverage. The adhesive-coated web 12 is then passed around drying drum 26 whereupon the adhesive-coated surface 14 becomes adhered to the roller 26. The first side 14 of the web 12 is then creped (i.e. lifted off the drum and bent) using doctor blade 28.

A second side 16 of the web 12 may be creped using the second creping station 30, regardless of whether or not the first creping station 20 has been bypassed. The second creping station 30 includes a second printing station including a lower patterned or smooth printing roller 32, an upper smooth anvil roller 34, and a printing bath 35, and also includes a dryer drum 36 and associated creping blade 38. The rollers 32 and 34 nip the web 12 and guide it forward. As the rollers 32 and 34 turn, the printing roller 32 dips into bath 35 containing adhesive material, and applies the adhesive to the second side 16 of the web 12 in a partial or total coverage. The adhesive-coated web 12 is then passed around drying roller 36 whereupon the adhesive-coated surface 16 becomes adhered to the roller 36. The second side 16 of the web 12 is then creped (i.e. lifted off the drum surface and bent) using doctor blade 38.

After creping, the nonwoven web 12 may be passed through a chilling station 40 and wound onto a storage roll 42. The level of creping is affected by the surface speed of the windup roll 42 relative to the surface speed of the creping drum 36, according to the equation presented above. The surface speed of the windup roll 42 is slower than the surface speed of the creping drum 36, and the difference between the two speeds affects the level of creping. The level of creping should generally be about 5–75%, preferably about 15–60%, most preferably about 25–50%.

The nonwoven web 12 may be any type of thermoplastic nonwoven web. For instance, web 12 may be a spunbonded web, a meltblown web, a bonded carded web, or a combination including any of the following. Preferably, the web 12 is a spunbonded web. A wide variety of thermoplastic polymer materials can be used to make the nonwoven web 12. Exemplary polymer materials include without limitation, polypropylene, polyethylene (high and low density), ethylene copolymers with $C_3$–$C_{20}$ α-olefins, propylene copolymers with ethylene or $C_4$–$C_{20}$ α-olefins, butene copolymers with ethylene, propylene, or $C_5$–$C_{20}$ α-olefins, polyvinyl chloride, polyesters, polyamides, polyfluorocarbons, polyurethane, polystyrene, polyvinyl alcohol, caprolactams, and cellulosic and acrylic resins. Bicomponent and biconstituent thermoplastic webs may also be utilized, as well as webs containing blends of one or more of the above-listed thermoplastic polymers. The web 12 may have a basis weight of about 0.2–2.0 ounces per square yard (osy) before creping, desirably about 0.3–1.5 osy.

A wide variety of adhesive bonding materials may be utilized to reinforce the fibers of the web 12 at the locations of adhesive application, and to temporarily adhere the web 12 to the surface of the drum 26 and/or 36. Elastomeric adhesives (i.e. materials capable of at least 75% elongation without rupture) are especially suitable. Suitable materials include without limitation aqueous-based styrene butadiene adhesives, neoprene, polyvinyl chloride, vinyl copolymers, polyamides, ethylene vinyl terpolymers and combinations thereof. The presently preferred adhesive material is an acrylic polymer emulsion sold by the B. F. Goodrich Company under the trade name HYCAR®. The adhesive may be applied using the printing technique described above or may, alternatively, be applied by meltblowing, melt spraying, dripping, splattering, or any technique capable of forming a partial or total adhesive coverage on the thermoplastic nonwoven web 12.

The percent adhesive coverage of the web 12 generally affects the level of creping obtained. Generally the adhesive should cover about 5–100% of the web surface, preferably about 10–70% of the web surface, more preferably about 25–50% of the web surface. In the presently preferred embodiment, the web 12 is coated with adhesive and creped on only one side. The web 12 may be coated with adhesive and creped on both sides, however. The adhesive should also penetrate the nonwoven web 12 in the locations where the adhesive is applied. Generally, the adhesive should penetrate through about 10–50% of the nonwoven web thickness, although there may be greater or less adhesive penetration at some locations.

The resulting creped nonwoven web product has a controlled pattern creping which corresponds generally to the nonwoven web interfilament bond pattern and, to a lesser degree, the applied adhesive material. A presently preferred nonwoven web bonding pattern is a regular point bond pattern referred to as the Hansen Pennings or "HP" pattern, shown in FIG. 5. The HP pattern has a bond area of 19–32%, a bond density of 204 points/in$^2$, and a point height or depth of 0.030 in. This bond pattern results in the formation of regular fiber loops and excellent bulk.

Figure 6:
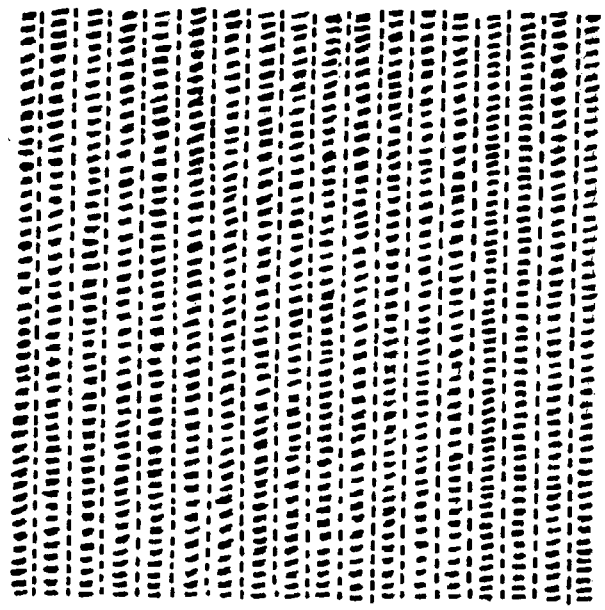

Another suitable nonwoven web bond pattern is the "rib knit" pattern shown in FIG. 6. The rib knit pattern is designed for a knitted fabric appearance. The pattern has a bond area of 10–20%, a bond density of 212 bond points/in$^2$, and a bond point height or depth of 0.044 in. This pattern provides creped nonwoven fabrics with excellent softness.

Figure 7:
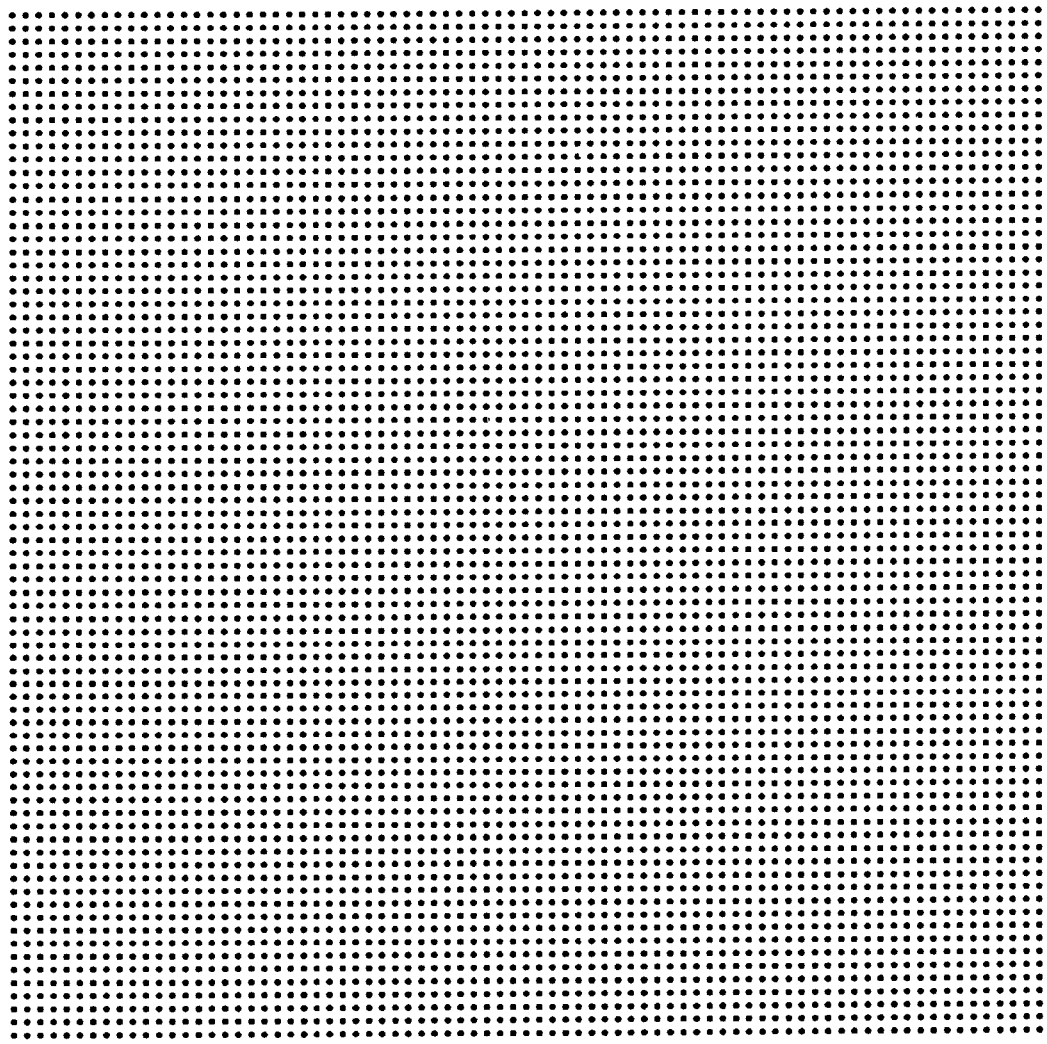

Another suitable nonwoven web bond pattern, characterized by elliptical-shaped point bonds, is the "wire weave" pattern shown in FIG. 7. The wire weave pattern has a bond area of 15–21%, a bond density of 302 point/in$^2$, and a bond point height or depth of 0.038 in. This pattern is designed to provide a nonwoven fabric with a woven look, and results in creped nonwoven fabrics having good softness, bulk, and fiber looping.

The creping of the nonwoven web is primarily manifested in the bonded areas of the base ("raw") nonwoven web, corresponding to the nonwoven web bond pattern. As a result of the creping, the bonded regions are bent out of plane so as to cause permanent creping of the web, and the formation of filament looped regions in the unbonded regions alternating with (in between) the creped bonded regions.

Figure 2:
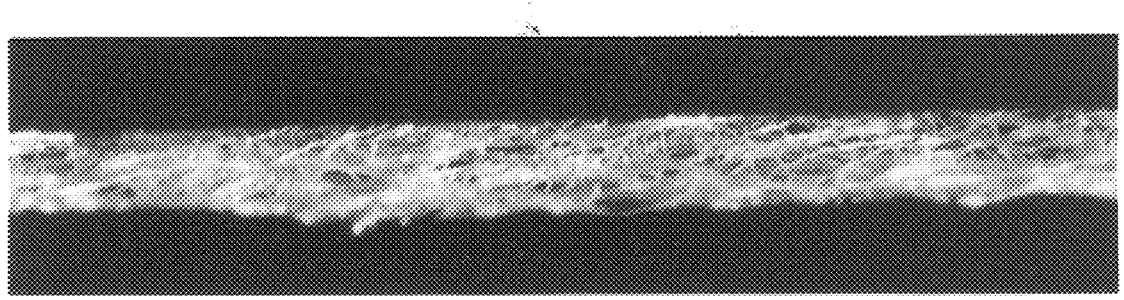
FIG. 2 is a greatly enlarged sectional view photograph of an uncreped nonwoven web.
Figure 3:
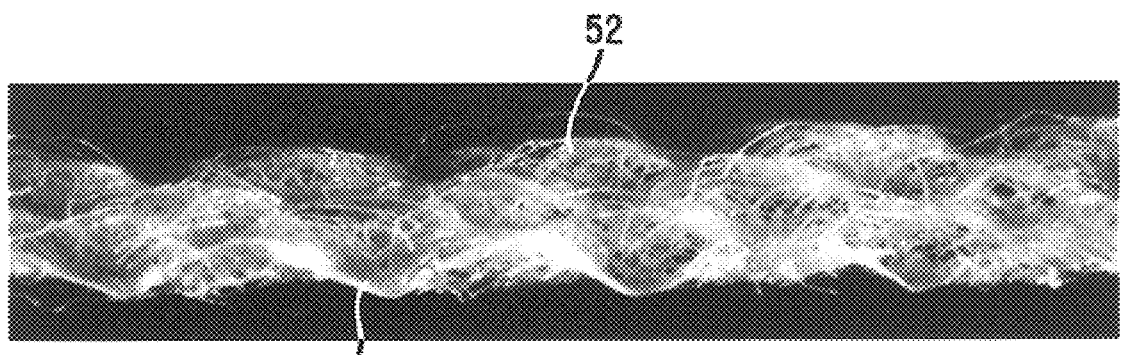
FIG. 3 is a greatly enlarged sectional view photograph of a permanently creped nonwoven web of the invention, creped on one side to a 25% crepe level.
Figure 4:
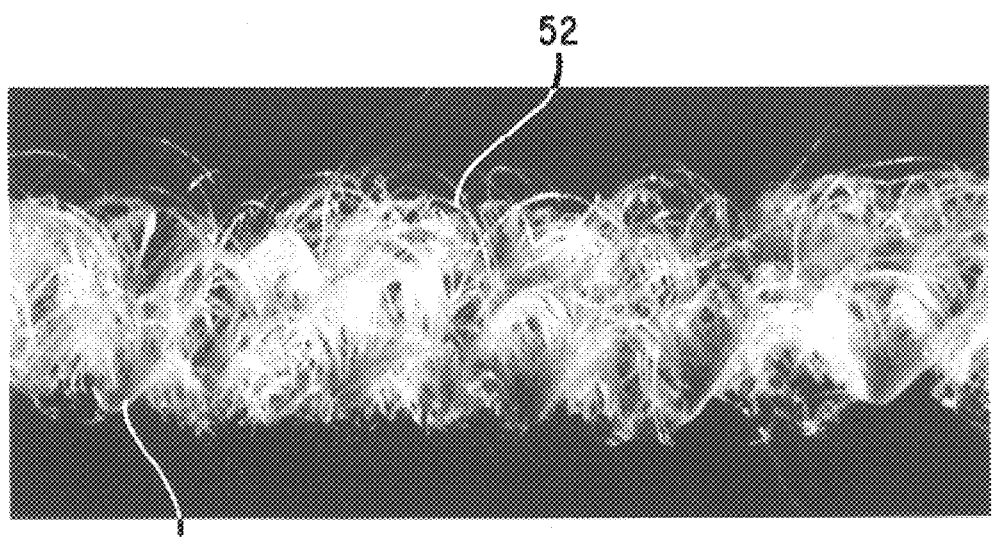
FIG. 4 is a greatly enlarged sectional view photograph of a permanently creped nonwoven web of the invention, creped on one side to a 50% crepe level.

FIG. 2 illustrates an uncreped nonwoven web, which is a spunbonded web. FIGS. 3 and 4 illustrate the same spunbonded web creped according to the invention at creping percentages of 25% and 50%, respectively. As shown in FIGS. 3 and 4, each of the creped webs has creped nonwoven web bond regions 50 which are bent permanently out of plane due to the creping. Looped regions 52 corresponding to the unbonded, non-creped regions exist between the creped regions. The creped regions 50 include tightly bonded filament regions, while the looped regions 52 include loose filament regions. The individual filament loops terminate at both ends in the adhesive-reinforced regions, and are anchored in the adhesive-reinforced regions. As seen in FIGS. 3 and 4, the degree of looping increases substantially when the level of creping is increased from 25% to 50%. The completeness of the loops suggest that there is very little fiber breakage.

The resulting creped nonwoven web has low density, high permeability, excellent surface and bulk softness, recoverable stretch properties, surface topology, and permanent out-of-plane fiber orientation. The creped nonwoven web can be used in a variety of end products including inkers, transfer and surge layers, outercovers, wipers, and other fluid handling materials. One excellent use of the creped nonwoven web is as an outercover component for a diaper. The creped nonwoven web may, for instance, be laminated to a breathable polyolefin film including a mixture of thermoplastic polymer, e.g. a polyolefin such as polyethylene or polypropylene, and a particulate filler, e.g. calcium carbonate. The film is permeable to water vapor but substantially impermeable to liquid water. The breathable film can be laminated to the creped nonwoven web using thermal bonding, adhesive bonding, and/or other bonding techniques well known in the art. The laminate is then positioned on the underside or backside of the absorbent core of a diaper with the film component facing the absorbent core. The creped nonwoven web component thus faces outward, contributing a soft, fluffy, bulky feel to the diaper.

Because of the looping caused in the uncreped, unbonded regions, the creped nonwoven web 12 is also highly suitable for use as the female ("loop") component in a hook-and-loop type fastener. The loops in the web 12 engage the male fastener components in a peelable fashion, such that the hook and loop fastener can be opened and closed a number of times.

In another embodiment, the nonwoven web can be mechanically stretched, preferably stretched in the machine direction (causing the web to contract or neck in the cross direction) before applying the adhesive and creping the web. The resulting necked web product is stretchable in the cross direction. Mechanical stretching of the web is accomplished using processes well known in the art. For instance, the web may be pre-stretched by about 0–100% of its initial length in the machine direction to obtain a necked web that can be stretched (e.g. by about 0–100%) in the cross direction. Preferably, the web is stretched by about 10–100% of its initial length, more commonly by about 25–75% of its initial length. The stretched web is then dimensionally stabilized to some extent, first by the adhesive which is applied to the web, and second by the heat which is imparted from the creping drum. This stabilization sets the cross-directional stretch properties of the web. The machine direction stretch is further stabilized by the out-of-plane deformation of the nonwoven web bonded areas that occurs during creping.

The pre-stretching of the web can be used to optimize and enhance physical properties in the creped nonwoven product including softness, bulk, stretchability and recovery, permeability, basis weight, density, and liquid holding capacity. The elastic behavior of the creped nonwoven web can be further enhanced by laminating it to a layer of elastic material, for example, an isotropic elastic web or a layer of elastic strands.

EXAMPLES

Figure 5:
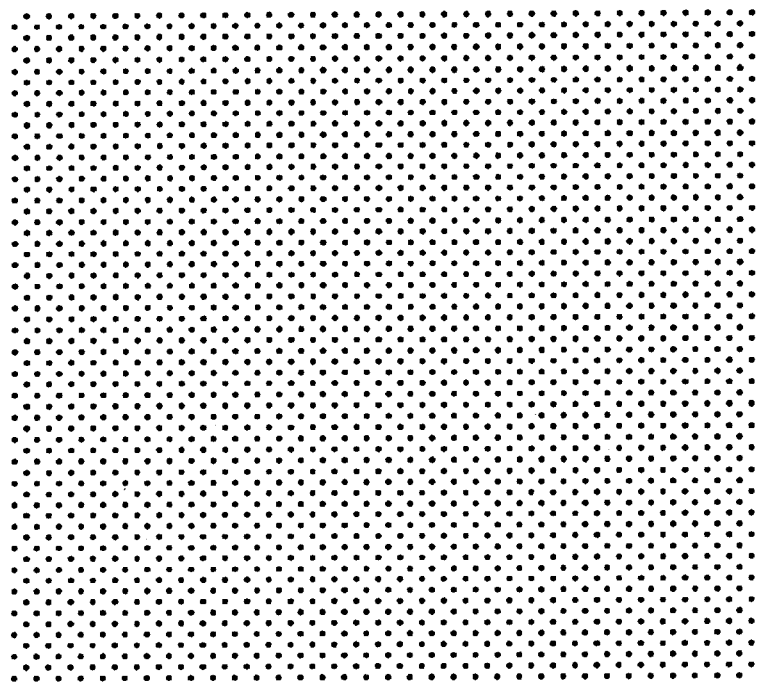
FIGS. 5–7 illustrate three nonwoven web bonding patterns used during preparation of the creped nonwoven web of the invention.

A polypropylene spunbonded web having an initial basis weight of 0.35 osy was subjected to a one-sided creping process as described above. The adhesive used was an acrylic polymer emulsion sold by the B. F. Goodrich Company under the trade name HYCAR®. The adhesive was applied at a 5% wet adhesive pick-up (based on the weight of the web) to different samples of the web using a printing process. The adhesive covered 15–20% of the web surface. The base nonwoven web was point-bonded with a HP adhesive pattern as illustrated in FIG. 5. Each sample was bonded to a drying drum and creped using a doctor blade using creping drum and wind-up roll speeds which yielded products with 10%, 25% and 50% crepe. The drum had a temperature of 180° F. The samples were measured for basis weight (mass divided by area covered the web), apparent density, true density, saturated capacity, thickness, mean pore radius, permeability, and pore volume. The pertinent measurement procedures are summarized below. The following results were achieved.

|  | Example 1 (No Crepe) | Example 2 (10% Crepe) | Example 3 (25% Crepe) | Example 4 (50% Crepe) |
| --- | --- | --- | --- | --- |
| Basis Weight | 0.35 osy | 0.39 osy | 0.45 osy | 0.56 osy |
| Apparent Density | 0.096 g/cc | 0.041 g/cc | 0.030 g/cc | 0.022 g/cc |
| True Density | 0.083 g/cc | 0.046 g/cc | 0.044 g/cc | 0.036 g/cc |
| Saturated Capacity | 10.0 g/g | 19.5 g/g | 20.7 g/g | 25.2 g/g |
| Thickness | 5 mils | 11 mils | 22 mils | 34 mils |
| Mean Pore Radius | 60 microns | 100 microns | 140 microns | 180 microns |
| Permeability | 250 darcies | 1000 darcies | 2100 darcies | 3500 darcies |
| Pore Volume at Mean Pore Radius | 240 cc/g | 390 cc/g | 460 cc/g | 480 cc/g |

As shown above, the creping substantially increased the bulk, permeability and volume of the fabric while reducing its densities. The permanently creped products had out-of-plane bonding in the creped areas and exhibited excellent softness, surface topographies, and recoverable stretchability.

The following measurement procedures can be used to generate this data. The basis weight is determined by measuring the mass of a creped nonwoven web sample and dividing it by the area covered by the nonwoven web sample. Generally, the basis weight increases at higher levels of creping due to crinkling and bulking of the web.

The apparent density is determined by measuring the weight of a creped nonwoven web sample and dividing it by the sample volume. The sample volume is calculated by multiplying the sample area by the sample thickness measured at 0.05 psi.

The saturated capacity is a measurement of the total liquid held by a saturated creped nonwoven web sample, and is reported in grams liquid per gram of creped nonwoven web. This can be determined using an apparatus based on the porous plate method reported by Burgeni and Kapur in the *Textile Research Journal*, Volume 37, pp. 356–366 (1967), the disclosure of which is incorporated by reference. The apparatus includes a movable stage interfaced with a programmable stepper motor, and an electronic balance controlled by a computer. A control program automatically moves the stage to a desired height, collects data at a specified sampling rate until equilibrium is reached, and then moves the stage to the next calculated height. Controllable parameters include sampling rates, criteria for equilibrium and the number of absorption/desorption cycles.

Data for this analysis were collected using mineral oil in desorption mode. That is, the material was saturated at zero height and the porous plate (and the effective capillary tension on the sample) was progressively raised in discrete steps corresponding to the desired capillary radius. The amount of liquid pulled out from the sample was monitored. Readings at each height were taken every fifteen seconds and equilibrium was assumed to be reached when the average change of four consecutive readings was less than 0.005 g. The interfacial liquid (at the interface between the saturated nonwoven web sample and the porous plate) was removed by raising the plate slightly (0.5 cm).

The true density of the material (grams/cc) represents the density of the interior structure and is determined from the saturated capacity (cc liquid/gram) and the density of the nonwoven fibers and/or particles.

$$\text{True density} = \frac{\text{fiber density}}{(\text{saturated capacity} \times \text{fiber density}) + 1}$$

The permeability (darcies) is obtained from a measurement of the resistance to flow of liquid by the material. A liquid of known viscosity is forced through the material of a given thickness at a constant flow rate and the resistance to flow, measured as a pressure drop, is monitored. Darcy's law is used to measure the permeability:

$$\text{Permeability (cm}^2) = \frac{\text{flow rate (cm/sec)} \times \text{thickness (cm)} \times \text{viscosity (pascal-sec)}}{\text{pressure drop (pascals)}}$$

wherein 1 darcy = $9.87 \times 10^{-9}$ cm$^2$

The mean pore radius and pore volume are measured using the same apparatus used to measure saturated capacity. Again, the procedure and apparatus are described further in the above-referenced article by Burgeni and Kapur, the disclosure of which is incorporated by reference.

While the embodiments of the invention disclosed herein are presently considered preferred, various improvements and modifications can be made without departing from the spirit and scope of the invention. The scope of the invention is indicated in the appended claims, and all changes that fall within the meaning and range of equivalents are intended to be embraced therein.

I claim:

1. A permanently creped thermoplastic nonwoven web comprising:
   a nonwoven fibrous web at least partially covered with a creping adhesive, the nonwoven fibrous web having permanently creped interfilament-bonded regions alternating with non-creped regions of no interfilament bonding;
   the nonwoven web having a nonwoven web bond pattern which effects the interfilament-bonded regions;
   the interfilament-bonded regions being creped so as to exhibit permanent out-of-plane bending;
   the regions of no interfilament bonding including a multiplicity of filament loops terminating in the interfilament-bonded regions.

2. The permanently creped thermoplastic nonwoven web of claim 1, having a level of creping of about 5–75%.

3. The permanently creped thermoplastic nonwoven web of claim 1, having a level of creping of about 15–60%.

4. The permanently creped thermoplastic nonwoven web of claim 1, having a level of creping of about 25–50%.

5. The creped thermoplastic nonwoven web of claim 1, comprising a nonwoven web selected from the group consisting of a spunbonded web, a meltblown web, a carded web, and combinations thereof.

6. The creped thermoplastic nonwoven web of claim 1, comprising a nonwoven spunbonded web.

7. The creped thermoplastic nonwoven web of claim 1, wherein the web comprises a polymer selected from the group consisting of propylene polymers and copolymers.

8. The creped thermoplastic nonwoven web of claim 1, wherein the web comprises a polymer selected from the group consisting of ethylene polymers and copolymers.

9. The creped thermoplastic nonwoven web of claim 1, wherein the web comprises a polymer selected from the group consisting of butene polymers and copolymers.

10. The creped thermoplastic nonwoven web of claim 1, wherein the creping adhesive comprises an elastomeric adhesive.

11. The creped thermoplastic nonwoven web of claim 1, wherein the creping adhesive comprises a material selected from the group consisting of styrene butadiene adhesives, neoprene, polyvinyl chloride, vinyl copolymers, polyamides, ethylene vinyl terpolymers, and combinations thereof.

12. The creped thermoplastic nonwoven web of claim 1, wherein the nonwoven fibrous web is mechanically stretched before the nonwoven fibrous web is at least partially covered with the creping adhesive.

13. The creped thermoplastic nonwoven web of claim 12, wherein the nonwoven fiber web is stretched in the machine direction before the nonwoven web is at least partially covered with the creping adhesive.

14. The creped thermoplastic nonwoven web of claim 12, wherein the nonwoven fibrous web is mechanically stretched by about 10–100% of an initial length of the nonwoven fibrous web before the nonwoven fibrous web is at least partially covered with the creping adhesive.

15. The creped thermoplastic nonwoven web of claim 12, wherein the nonwoven fibrous web is mechanically stretched by about 25–75% of an initial length of the nonwoven fibrous web before the nonwoven fibrous web is at least partially covered with the creping adhesive.

16. The permanently creped thermoplastic nonwoven web of claim 1, wherein the nonwoven web bond pattern comprises an HP pattern.

17. The permanently creped thermoplastic nonwoven web of claim 1, wherein the nonwoven web bond pattern comprises a rib knit pattern.

18. The permanently creped thermoplastic nonwoven web of claim 1, wherein the nonwoven web bond pattern comprises a wire weave pattern.

19. The permanently creped thermoplastic nonwoven web of claim 1, wherein the creping adhesive comprises a vinyl copolymer.

20. The permanently creped thermoplastic nonwoven web of claim 1, wherein the creping adhesive comprises an ethylene vinyl terpolymer.

21. A female component for a hook-and-loop fastener, comprising:
   a permanently creped thermoplastic nonwoven web at least partially covered with a creping adhesive, the web having permanently creped interfilament-bonded regions bent out of plane, and non-creped regions of no interfilament bonding between the creped interfilament-bonded regions;

the nonwoven web having a nonwoven web bond pattern which effects the interfilament-bonded regions;

the regions of no interfilament bonding including a multiplicity of filament loops anchored at both ends in the creped regions.

22. The female fastener component of claim 21, wherein the thermoplastic nonwoven web is creped on one side thereof.

23. The female fastener component of claim 21, wherein the thermoplastic nonwoven web is creped twice, once on each side thereof.

24. The female fastener component of claim 21, wherein the creped thermoplastic nonwoven web has a level of creping of about 5–75%.

25. The female fastener component of claim 21, wherein the creped thermoplastic nonwoven web has a level of creping of about 15–60%.

26. The female fastener component of claim 21, wherein the creped thermoplastic nonwoven web has a level of creping of about 25–50%.

27. The female fastener component of claim 21, wherein the thermoplastic nonwoven web comprises a material selected from the group consisting of spunbonded webs, meltblown webs, carded webs, and combinations thereof.

28. The female fastener component of claim 21, wherein the thermoplastic nonwoven web comprises a spunbonded web.

29. The female fastener component of claim 21, wherein the nonwoven web bond pattern comprises an HP pattern.

30. The female fastener component of claim 21, wherein the nonwoven web bond pattern comprises a rib knit pattern.

31. The female fastener component of claim 21, wherein the nonwoven web bond pattern comprises a wire weave pattern.

32. An outercover material, comprising:

a permanently creped thermoplastic nonwoven web at least partially covered with a creping adhesive, the web having permanently creped interfilament-bonded regions bent out of plane, and non-creped regions of no interfilament bonding between the creped regions;

the nonwoven web having a nonwoven web bond pattern which effects the interfilament-bonded regions; and a moisture permeable, substantially liquid impermeable polymer-based film laminated to the creped thermoplastic nonwoven web.

33. The outercover material of claim 32, wherein the nonwoven web is creped on one side thereof.

34. The outercover material of claim 32, wherein the nonwoven web comprises a material selected from the group consisting of a spunbonded web, a meltblown web, a carded web, and combinations thereof.

35. The outercover material of claim 32, wherein the nonwoven web comprises a spunbonded web.

36. The outercover material of claim 32, wherein the film comprises a mixture of a polymer and a particulate filler.

37. The outercover material of claim 36, wherein the film polymer comprises a polyolefin.

38. The outercover material of claim 32, wherein the nonwoven web bond pattern comprises an HP pattern.

39. The outercover material of claim 32, wherein the nonwoven web bond pattern comprises a rib knit pattern.

40. The outercover material of claim 32, wherein the nonwoven web bond pattern comprises a wire weave pattern.

* * * * *